(12) United States Patent
Lavigne et al.

(10) Patent No.: US 10,273,339 B2
(45) Date of Patent: Apr. 30, 2019

(54) SYNTHESIS OF A HIGHLY CRYSTALLINE, COVALENTLY LINKED POROUS NETWORK

(71) Applicants: John J. Lavigne, Columbia, SC (US); R. William Tilford, Kingsport, TN (US)

(72) Inventors: John J. Lavigne, Columbia, SC (US); R. William Tilford, Kingsport, TN (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/479,414

(22) Filed: Sep. 8, 2014

(65) Prior Publication Data

US 2015/0065596 A1 Mar. 5, 2015

Related U.S. Application Data

(62) Division of application No. 13/562,697, filed on Jul. 31, 2012, now Pat. No. 8,829,065, which is a division of application No. 12/279,006, filed as application No. PCT/US2007/004802 on Feb. 23, 2007, now Pat. No. 8,258,197.

(60) Provisional application No. 60/776,707, filed on Feb. 24, 2006.

(51) Int. Cl.
*C08J 9/00* (2006.01)
*C07F 5/02* (2006.01)

(52) U.S. Cl.
CPC .......... *C08J 9/00* (2013.01); *C07F 5/025* (2013.01); *C08J 2485/04* (2013.01)

(58) Field of Classification Search
CPC ........................................... C08J 9/00
USPC ............................................ 521/152
See application file for complete search history.

(56) References Cited

U.S. PATENT DOCUMENTS

| 6,228,818 B1 | 5/2001 | Schwind et al. |
| 2006/0089265 A1 | 4/2006 | Hanes, Jr. et al. |
| 2006/0154807 A1 | 7/2006 | Yaghi et al. |

OTHER PUBLICATIONS

Tilford et al; Fcile synthesis—boronate network; American Chemcial Society; Chemistry of Materials (2006), 18(22), 5296-5301; Chem Abstract 146:45803.*
Koumoto, K.; Yamashita, T.; Kimura, T.; Luboradzki, R.; Shinkai, S. TEM and SEM Observations of Super-Structure Constructed in Organogel Systems from a Combination of Boronic-Acid-Appended Bola-Amphiphiles with Chiral Diols. *Nanotechnology*, Dec. 25-31, 2001.

(Continued)

*Primary Examiner* — Duc Truong
(74) *Attorney, Agent, or Firm* — Dority & Manning, P.A.

(57) ABSTRACT

Porous networks are described linked by boronates. Also described are processes for producing the porous networks. The porous networks are formed by reacting a polyboronic acid with itself or with a polydiol, a polydiamine, or a polyamino alcohol. The resulting boronate linkage is covalently bonded. The characteristics and properties of the resulting porous material can be varied and altered by changing the reactants and by incorporating functional groups into the reactants. Of particular advantage, the porous materials can be formed at or near atmospheric pressure and at low temperature in the presence of one or more solvents.

8 Claims, 18 Drawing Sheets

Synthesis of the key building block to CPN-1, benzene-1,3,5-triboronic acid (1).

1

(56) References Cited

OTHER PUBLICATIONS

Nakazawa, I.; Suda, S.; Masuda, M.; Asai, M.; Shimizu, T. pH-Dependent Reversible Polymers Formed from Cyclic Sugar-and Aromatic Boronic Acid-Based Bolaamphiphiles. *Chem. Commun.* 2000, 881-882.

Kimura, T.; Yamashita, T.; Koumoto, K.; Shinkai, S. "Super-Structures can be Constructed in Organogels from Combination of Boronic-Acid-Appended Bolaamphiphile with Chiral Diols." *Tetrahedron Lett.* 1999, 40, 6631-6634.

Kimura, T.; Shinkai, S. "Chirality-Dependent Gel Formation from Sugars and Boronic-Acid-Appended Chiral Amphiphiles." *Chem. Lett.* 1998, 1035-1036.

Kimura, T.; Takeuchi, M.; Shinkai, S. "Saccharide Induction of Chiral Orientations of the Aggregate Formed from Boronic-Acid-Appended Amphiphiles," *Bull. Chem. Soc. Jpn.* 1998, 71, 2197-2204.

Mikami, M.; Shinkai, S. "Synthesis of Helical Polymers by Polycondensation of Diboronic Acid and Chiral Tetrols." *Chem. Lett.* 1995, 603-604.

Mikami, M.; Shinkai, S. "Synthesis of Sugar-Containing Polymers by Self-Condensation with Diboronic Acid."*J. Chem. Soc., Chem. Commun.* 1995, 153-154.

Ungurenaş u, C.; Cihodaru, S.; Popescu, I. "Nouveaus polyméres inorganiques et élément-organiques contenant bore et azote." *Tetrahedron Lett.* Oct. 1969, 1435-1438.

Musina, E. I.; Litvinov, I. A.; Balueva, A. S.; Nikonov, G. N. "New Phosphino-1,2,3-dioxaborinanes." *Russ. J Gen. Chem.* 1999, 69, 413-420.

Mulvaney, J. E.; Bloomfield, Jordan J.; Marvel, C. S. "Poly(benzborimidazolines)." *J. Polym. Sci.* 1962, 62 59-72.

Qin, Y.; Cheng, G.; Achara, O.; Parab, K.; Jakle, F. "A New Route to Organoboron Polymers via Highly Selective Polymer Modification Reactions." *Macromolecules* 2004, 37, 7123-7131.

Shoji, E.; Freund, M. S. "Potentiometric Saccharide Detection Based on the $pK_a$ Changes of Poly(aniline boronic acid)." *J. Am. Chem. Soc.* 2002, 124, 12486-12493.

Kuivila, H. G.; Keough, A. H.; Soboczenski, E. J. "Areneboronates from Diols and Polyols" *J. Org. Chem.* 1954, 19, 780-783.

Kobayashi, H.; Amaike, M.; Koumoto, K.; Shinkai, S. "Organization of Nucleosides Supported by Boronic Acid-Appended Poly(L-Lysine): Creation of a Novel RNA Mimic." *Bull. Chem. Soc. Jpn.* 2001, 74, 1311-1317.

Fournier, J.H.; Maris, T.; Wuest, J.D.; Guo, W.; Galoppini, E. "Molecular Tectonics. Use of the Hydrogen Bonding of Boronic Acids to Direct Supramolecular Construction." *J. Am. Chem. Soc.* 2003, 125, 1002-1006.

International Search Report PCT/US07/04802, mailed Aug. 4, 2008.

* cited by examiner

Synthesis of the key building block to CPN-1, benzene-1,3,5-triboronic acid (1).

Derivatization of compound 1 to the corresponding neopentaglycol boronate ester.

Solved x-ray crystal structure of the neopentaglycol ester of benzene-1,3,5-tiboronic acid (1). Two conformational isomers were found to be present in the crystal in nearly a 1:1 ratio.

Conformation "A". Displacement ellipsoids drawn at the 30% probability level.

Conformation "B". Displacement ellipsoids drawn at the 30% probability level.

SYNTHESIS OF A HIGHLY CRYSTALLINE, COVALENTLY LINKED POROUS NETWORK

RELATED APPLICATIONS

The present application is a divisional of and claims priority to U.S. patent application Ser. No. 13/562,697 titled "Synthesis of a Highly Crystalline, Covalently Linked Porous Network" of Lavigne, et al. filed on Jul. 31, 2012 now U.S. Pat. No. 8,829,065; is a divisional of and claims priority to U.S. patent application Ser. No. 12/279,006 of Lavigne, et al. filed on Feb. 9, 2009 (now U.S. Pat. No. 8,258,197), which is a nationalization of International Patent Application No. PCT/US07/04802 filed on Feb. 23, 2007; and claims priority to U.S. Provisional Patent Application No. 60/776,707, filed on Feb. 24, 2006, all of which are incorporated by reference herein.

FEDERALLY SPONSORED RESEARCH

The present invention was developed with funding from the National Science Foundation under grant number CHE 0415553 and the American Chemical Society-Petroleum Research Fund under grant number 41833-G4.

BACKGROUND (1) Field of the Invention

The present invention relates to the field of synthesizing crystalline, covalently linked porous networks with high surface area.

(2) Description of the Related Art

Porous materials are of great interest for applications in gas storage, catalysis and separations. Therefore, the ability to generate highly porous, robust materials in an efficient and simple manner is greatly desired. Metal-organic coordination networks have been vigorously investigated as a means to generate microporous frameworks. While there have been numerous successes using this approach, it would be beneficial to have a means to assemble covalently linked networks for the generation of more structurally stable assemblies. Highly ordered, porous networks based on boronic acid building blocks have been previously disclosed. However, these materials assemble through hydrogen bonding to form stable, highly interpenetrating, diamondoid frameworks. Further improvements in forming porous networks from boronic acids is still needed. In particular, a need exists for a porous network that is based on more stable covalent bonding. Also needed is an improved process for producing the porous networks that does not have high energy requirements.

SUMMARY

In general, the present disclosure is directed to an improved method of synthesizing and characterizing highly crystalline, covalently linked, porous organic networks under mild conditions. In one embodiment, for instance, the porous network is formed from a boronate linked network. According to the present disclosure, for instance, porous networks can be formed from dioxaborole, diazaborole, oxazaborole, or boroxine (or anhydride) linked networks.

The porous networks formed in accordance with the present disclosure can be used in numerous applications. For instance, the porous product can be used to reversibly absorb gases or other chemical species, such as organic compounds. The porous networks can also be used as a catalyst or to support a catalyst during any suitable chemical reaction.

In one embodiment, for instance, a boronate porous network is formed according to the present disclosure by reacting and combining together a first reactant with a second reactant. The first reactant comprises a polyboronic acid or an acyclic boronate ester thereof. For instance, the first reactant may comprise a diboronic acid, a triboronic acid, a tetraboronic acid, or the like. The second reactant, on the other hand, may comprise a polydiol, a polyamino alcohol, or a polydiamine. As used herein, the prefix "poly" means two or more. The first reactant is reacted with the second reactant to form a covalently bonded polymeric or oligomeric porous network comprising a boronate linked network.

Of particular advantage, the present inventors have discovered that, in one embodiment, the above reaction can occur at or near atmospheric pressure and at a temperature of less than about 110° C. As used herein, at or near atmospheric pressure depends upon various factors including the particular reactants used and the temperature at which the reaction takes place. At or near atmospheric pressure, however, at least is from about 0.75 atmospheres to about 1.25 atmospheres.

Thus, the porous networks of the present disclosure can be formed economically and under moderate conditions. The temperature at which the porous network is formed, for instance, can be from about 15° C. to about 100° C., such as from about 20° C. to about 90° C. During formation of the porous network, the second reactant as described above may be added in excess in order to prevent the first reactant from reacting with itself if desired.

During formation of the porous network, at least one solvent may be present. For example, a first solvent may be present that has a boiling point of less than about 110° C. For instance, the first solvent may comprise tetrahydrofuran. A second solvent may also be present that may, for instance, improve the solubility of the polyboronic acid. The second solvent may also aid enhancing the fidelity of the product network by allowing the growing network to repair errors that may occur during synthesis given the reversibility of the boronate linkages. The second solvent may comprise, for instance, a low molecular weight alcohol. For instance, the second solvent may be methanol. The methanol may be present in an amount less than about 10% by volume, such as less than about 3% by volume.

As will be described in more detail below, various different polyboronic acids may be used to form the porous network. In addition, various different polydiols, various different polyamino alcohols, and various different polydiamines may also be used. In fact, the reactants can be selected so as to control the physical properties of the resulting product.

In one particular embodiment, a triboronic acid, such as benzene-1,3,5-triboronic acid may be reacted with a bis-diol. The bis-diol may comprise, for instance, 1,2,4,5-tetrahydroxybenzene.

The resulting product can be in the form of porous sheets stacked together. In one embodiment, the stacks of sheets may be arranged together such that the pores between adjacent sheets are in alignment. In this manner, a porous network is formed having channels that extend through the stacked sheets. The diameter of the pores can vary depending upon various factors. For instance, the pore diameter may be less than about 200 angstroms, such as less than about 70 angstroms, such as even less than about 20 angstroms. Of particular advantage, the resulting pore structure can be thermally stable at temperatures of at least about 500° C. The porous boronate linked network can have a surface area of greater than about 400 m²/g, such as greater than about 1200 m²/g. The surface area, however, can vary depending upon the particular reactants that are selected.

In an alternative embodiment, a porous network may be formed according to the present disclosure by reacting one or more polyboronic acids together. In this embodiment, a porous network is formed containing boroxine linkages. For instance, in one embodiment, a boroxine porous network may be formed by reacting a triboronic acid with itself. In particular, a dehydration product is formed by reacting the boronic acid with itself. Ultimately, an anhydride network is formed having a relatively small pore size.

Other features and aspects of the present disclosure are discussed in greater detail below.

BRIEF DESCRIPTION OF THE DRAWINGS

The present disclosure may be better understood with reference to the following figures.

DETAILED DESCRIPTION

Figure 1:
FIG. 1 is a schematic diagram showing one embodiment for a process for producing a triboronic acid.

It is to be understood by one of ordinary skill in the art that the present discussion is a description of exemplary embodiments only, and is not intended as limiting the broader aspects of the present invention.

The generation of self-assembling materials based on the interactions between poly-boronic acids and poly-diol compounds forming boronate linked materials represents one method to generate stable, highly crystalline porous covalent networks through a simple dehydration process without the need for the addition of catalysts or other reagents. Given the covalent yet reversible nature of the boronate linkage, these assemblies form in a highly ordered manner. Compared to other covalently bonded organic counterparts, boronate-linked networks are assembled with greater ease and with higher efficiency; furthermore, compared to their non-covalently bonded equivalents, the boronate-linked materials display enhanced stability.

Boronate linked porous networks have self-repairing capabilities and may comprise self-assembling crystalline networks. Described below is an assembly motif for the porous material. Through characterization it has been found that the boronate linked networks produce a highly crystalline, covalent, microporous extended organic network that can be synthesized in good yields under moderate conditions. In one embodiment, the network may be assembled solely with boronate ester linkages.

In general, the porous networks of the present disclosure are formed by reacting a first reactant with a second reactant. The first reactant may comprise, for instance, a polyboronic acid. The second reactant, on the other hand, may vary depending upon the particular application and the desired results. The second reactant reacts with the first reactant to form a porous network, for example, linked through boronate esters. In one embodiment, the second reactant may comprise a polydiol for forming a porous network linked through a dioxaborole. In an alternative embodiment, the second reactant may comprise a polydiamine for producing a porous network linked through diazaboroles. In still another embodiment, the second reactant may comprise a polyamino alcohol for producing a porous network linked through oxazaboroles. In still another embodiment, the second reactant may comprise the same or a different polyboronic acid for producing a porous network linked by boroxines (or boronanhydrides). When producing these boronate linked networks of the present disclosure, the polyboronic acid may first be converted to an acyclic boronate ester prior to reacting with the second reactant.

Through the above process, a covalently bonded polymeric or oligomeric porous network containing boronate linkages is formed. It has been discovered that the covalent bonding interaction is also reversible between the boronic acids and the second reactant. In addition, the reactants can be varied in order to produce a porous network having desired properties and characteristics.

The boronate linked networks made according to the present disclosure provide various advantages and benefits. For instance, the boronate linked networks are more stable than other self-assembling interactions, such as porous networks that rely on hydrogen bonding. Yet, the acids/ester equilibrium of the boronate linked networks is reversible and retains all the benefits of a self-assembling system including self-repair, efficient formation, and the like.

The boronate linked networks are also hydrolytically labile and are thermally stable. In particular, even though unhindered boronates degrade hydrolytically, sterically crowded boronates exhibit increased stability. The boronate linked networks made according to the present disclosure, for instance, are thermally stable at temperatures of at least 400° C., such as at least 500° C. In addition, the material can be repaired thermally when degraded. Also of advantage, changing the nature or valency of the building blocks used to form the boronate linked networks readily alters the assembled product outcome and properties in a predictable fashion. Thus, porous networks can be formed according to the present disclosure that are tailored for a particular application.

In addition, as will be described in greater detail below, functional groups can be easily incorporated into the porous network. For instance, cyclic boronate esters quantitatively replace acyclic, mono-esters, thus other Lewis basic functionality can be incorporated into the esters during formation. The functionality may comprise, for instance, amines, alcohols, thiols, and the like.

The boronate linked porous networks of the present disclosure can be made using various techniques and methods. In one particular embodiment, for instance, the boronate linked networks may be formed through a facile dehydration process in one or more solvents. In particular, the present inventors have discovered that porous boronate linked networks can be formed by simply warming the reactants in the presence of a solvent. For example, the compound selected to be reacted with the polyboronic acid may, in one embodiment, be first combined with one or more solvents. For example, the reactant, such as a polydiol, may be first combined with a relatively low boiling point solvent in addition to a solvent that better solubilizes the polyboronic acid. The relatively low boiling point solvent, for instance, may comprise any suitable solvent that has a boiling point of less than about 100° C. For instance, in one embodiment, tetrahydrofuran may be used. Alternatively, water may be present.

The other solvent, on the other hand, may comprise any suitable alcohol. For instance, the alcohol may be a relatively low molecular weight alcohol, such as methanol, ethanol, a propanol or mixtures thereof. The solvents may be present during the reaction in an amount less than about 10% by volume, such as in an amount from about 1% to about 3% by volume.

Next, a polyboronic acid may then be combined with the solution in controlled amounts. In some embodiments, heat may be required for the reaction to proceed. Of particular advantage, however, the reaction can occur at or near atmospheric pressure and at a temperature of less than about 100° C., such as from about 15° C. to about 90° C., such as from about 20° C. to about 70° C.

As described above, in one embodiment, the compound to be reacted with the polyboronic acid may first be combined with a solvent prior to being contacted with the polyboronic acid. In other embodiments, however, it should be understood that the reaction can also be done by dissolving each reactant independently and mixing these solutions or by mixing the two reactants together and then adding the one or more solvents.

In one embodiment, the reactant that reacts with the polyboronic acid may be present in excess amounts so as to prevent the polyboronic acid from reacting with itself. As will be described below, however, when producing boroxines in accordance with the present disclosure, the first and second reactants both comprise polyboronic acids.

If desired, the polyboronic acid may first be converted to an acyclic boronate ester prior to or during the reaction.

In one embodiment, the reaction can occur in an inert atmosphere so as to prevent any undesired reactions occurring with oxygen. The inert atmosphere, for instance, may comprise any atmosphere having low levels of molecular oxygen. For instance, in one embodiment, the reaction can occur under nitrogen.

It is believed that the reactants undergo a condensation reaction to form the covalently bonded boronate linked porous network. When reacting a polyboronic acid with a polydiol, the molar ratio between the polyboronic acid and the polydiol may be from about 2:3 to about 1:2.5.

In general, any suitable polyboronic acid may be used to form porous networks in accordance with the present disclosure. In one particular embodiment, for instance, a triboronic acid may be used. In other embodiments, however, a diboronic acid or a tetraboronic acid may also be used. A non-exhaustive list of examples of polyboronic acids that may be used in the present disclosure include the following:

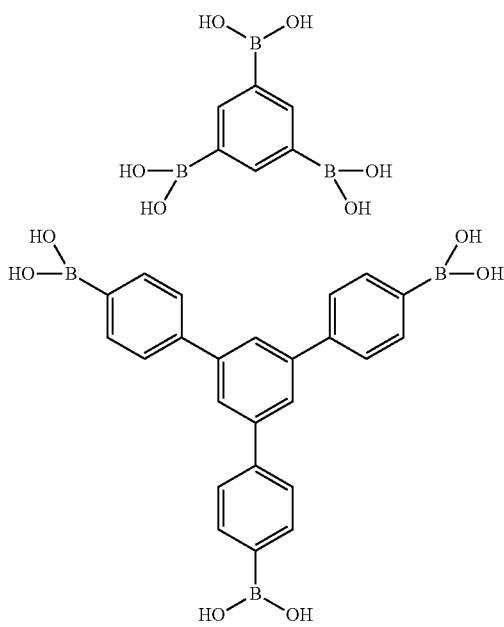

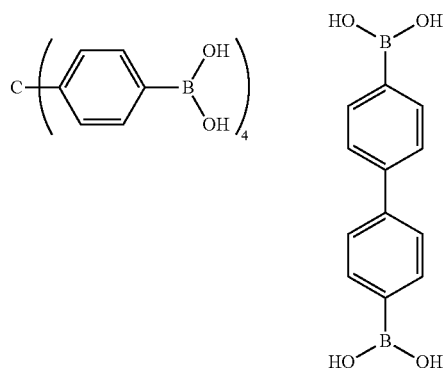

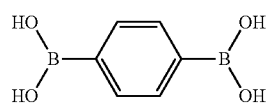

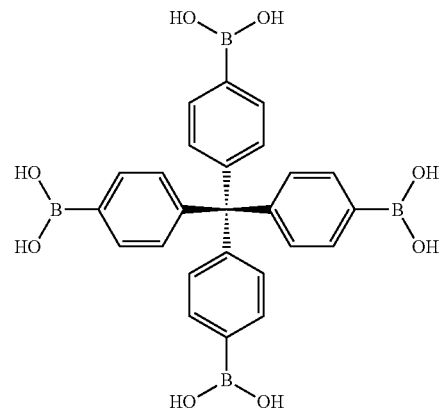

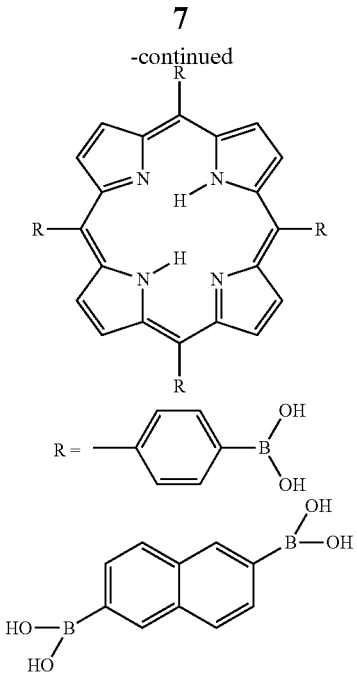

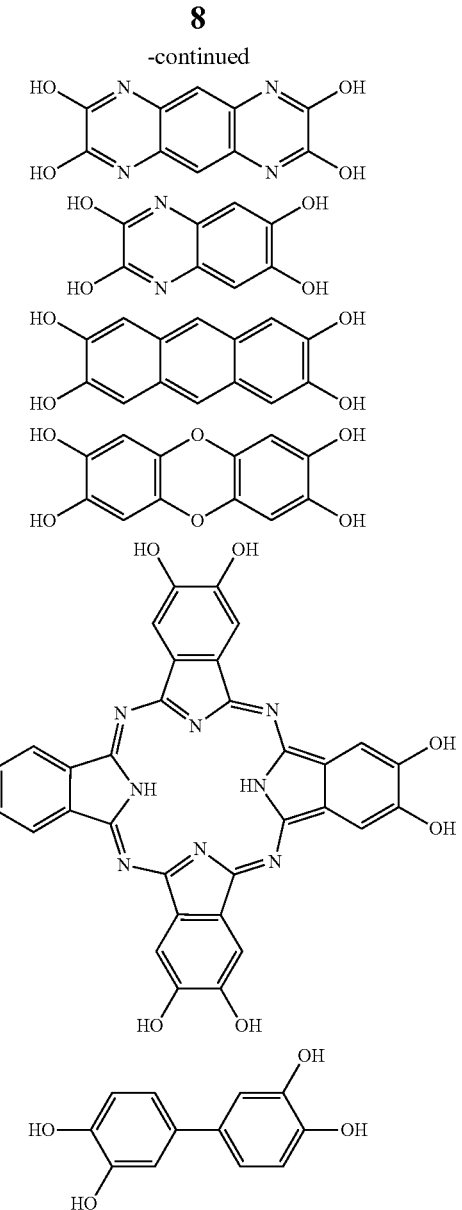

Boronic acids are also disclosed in U.S. Patent Application Publication No. 2006/0154807, which is incorporated herein by reference for all purposes.

Figure 15:
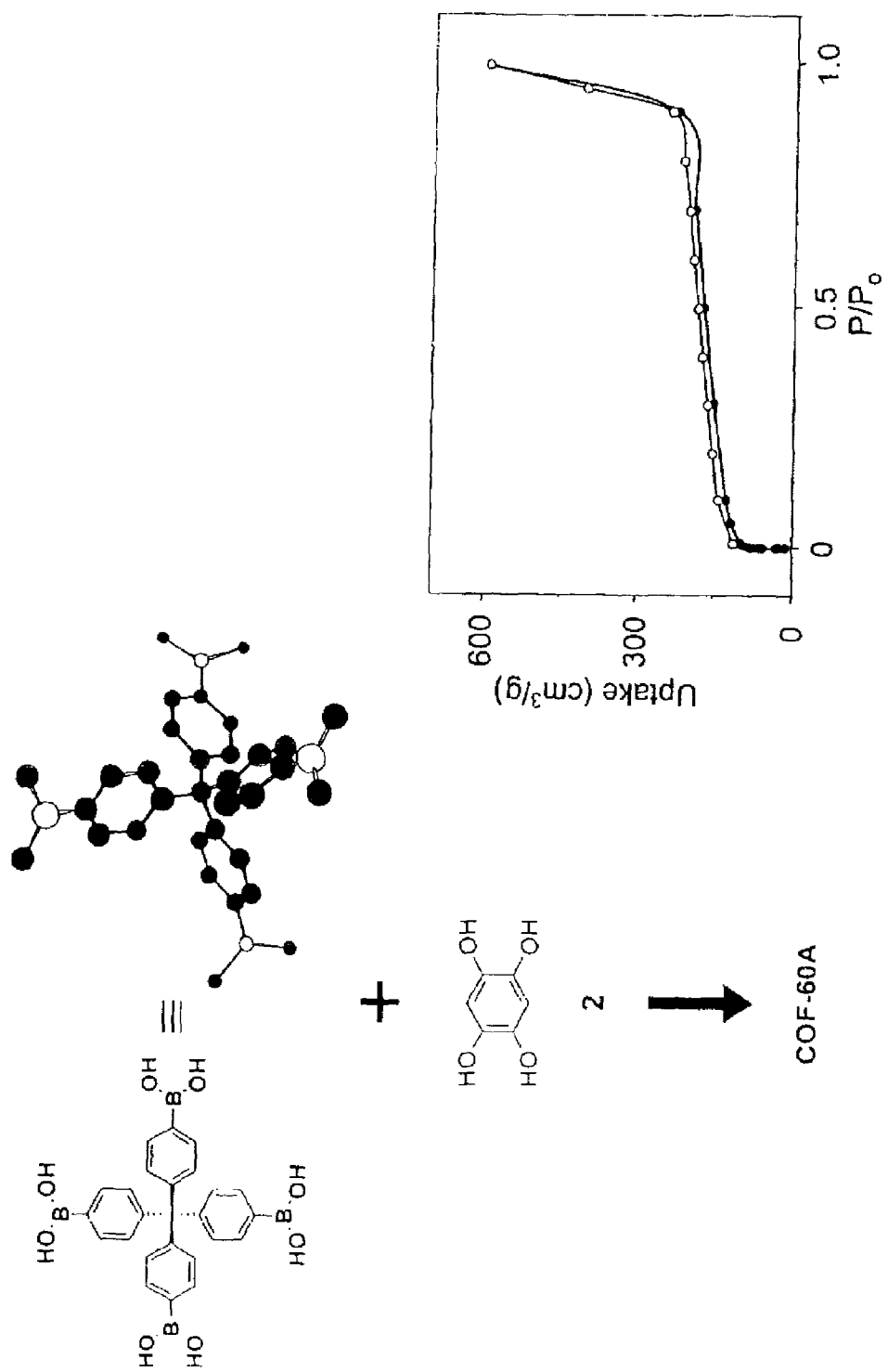
FIG. 15 is a schematic diagram of a tetraboronic acid and of one embodiment of a reaction scheme for producing a porous network in accordance with the present disclosure and gas adsorption data signifying this is a porous network.

When using a tetraboronic acid, it is believed that a diamondoid network may be formed due to the 3-dimensional configuration of the boronic acid. For example, referring to FIG. 15, a tetraboronic acid is shown that may be reacted with a bis-diol to produce a porous network. A gas adsorption profile for the resulting porous network is also illustrated in FIG. 15. In particular, the graph illustrates a molecular nitrogen gas adsorption isotherm for the resulting network when using 1,2,4,5-tetrahydroxybenzene. It is believed that this particular porous network made according to the present disclosure is crystalline and has a surface area of from about 400 m$^2$/g to about 500 m$^2$/g.

When using various other boronic acids, on the other hand, a more 2-dimensional structure is formed in sheets. Each sheet includes pores. As the different sheets stack together, it is believed that the pores align forming channels as will be described in greater detail below.

As described above, in one embodiment, the polyboronic acid may be reacted with a polydiol to form a porous network comprising dioxaborole linkages. In general, any suitable polydiol may be combined and reacted with the polyboronic acid. Examples of suitable polydiols include, without limitation, the following:

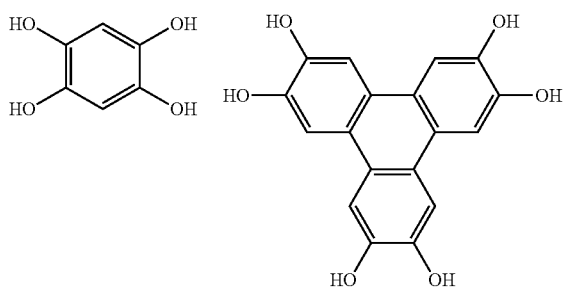

Figure 4:
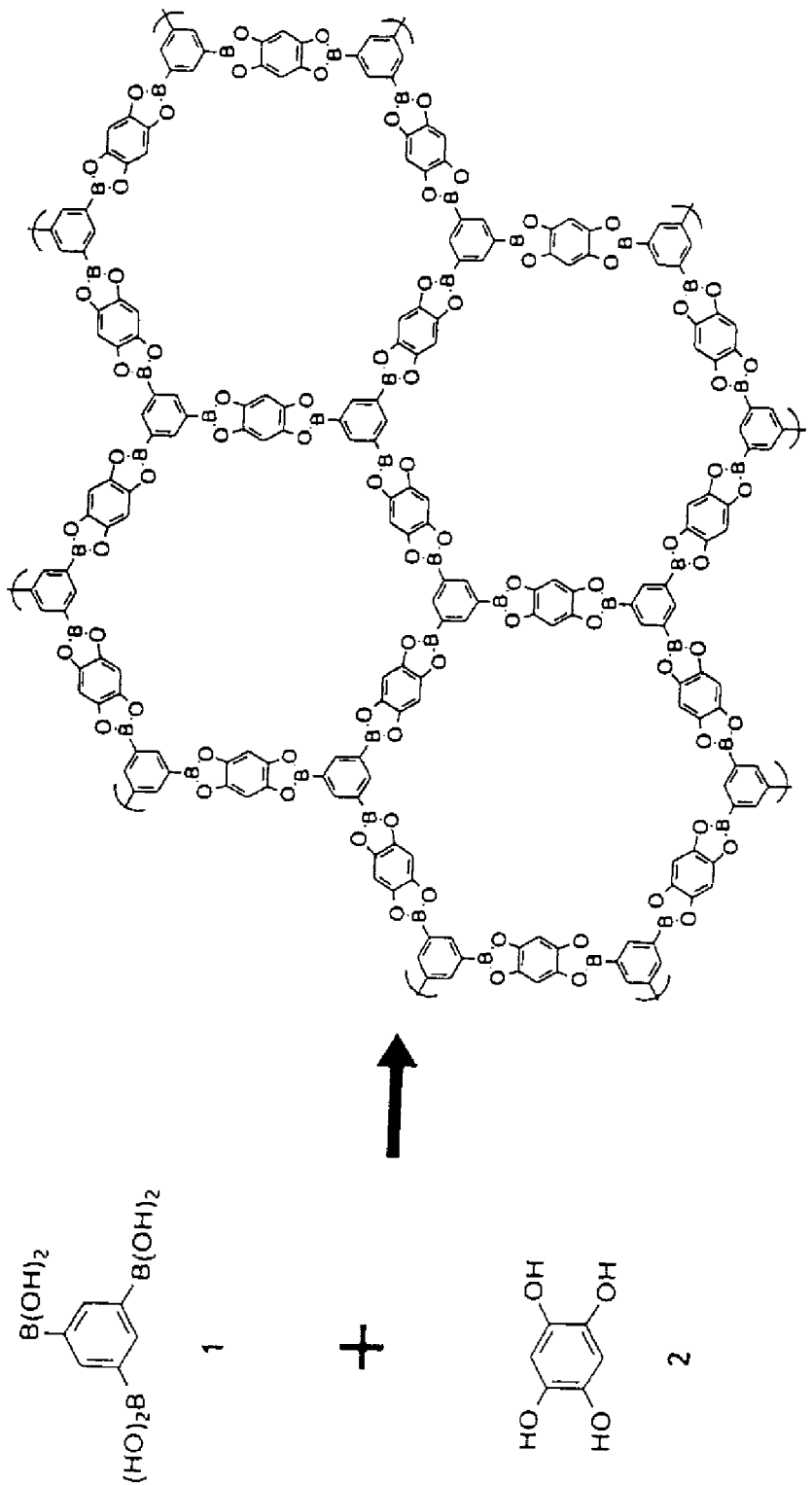
FIG. 4 is a schematic diagram of one embodiment of a reaction for forming porous networks in accordance with the present disclosure.
Figure 5:
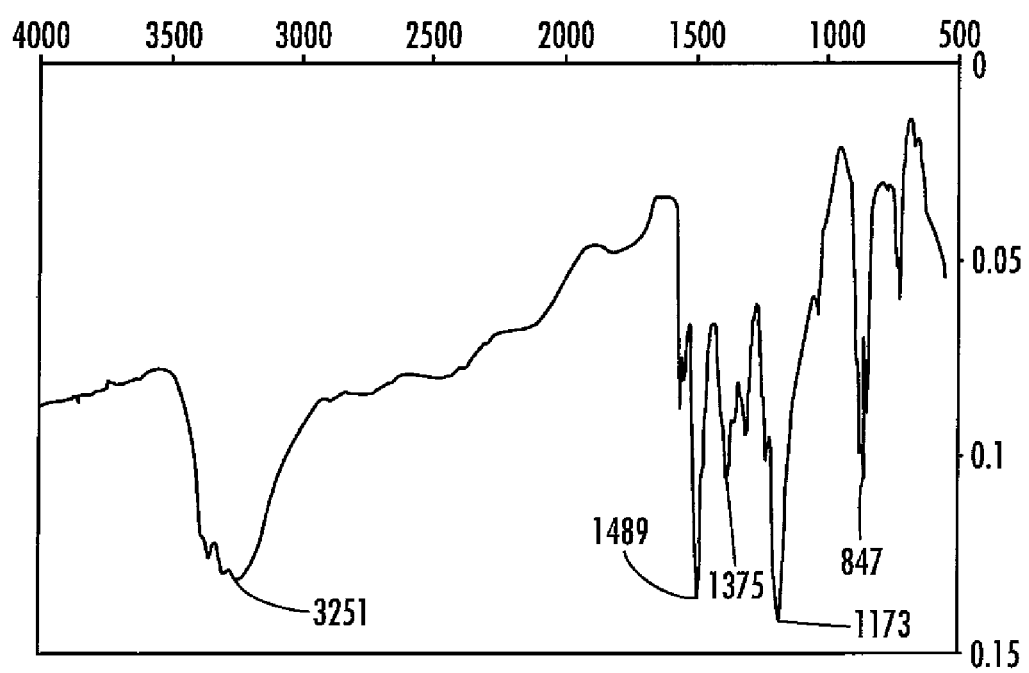
FIGS. 5 through 14 depict the characterization results for the starting materials and products for the network produced in FIG. 4.
Figure 6:
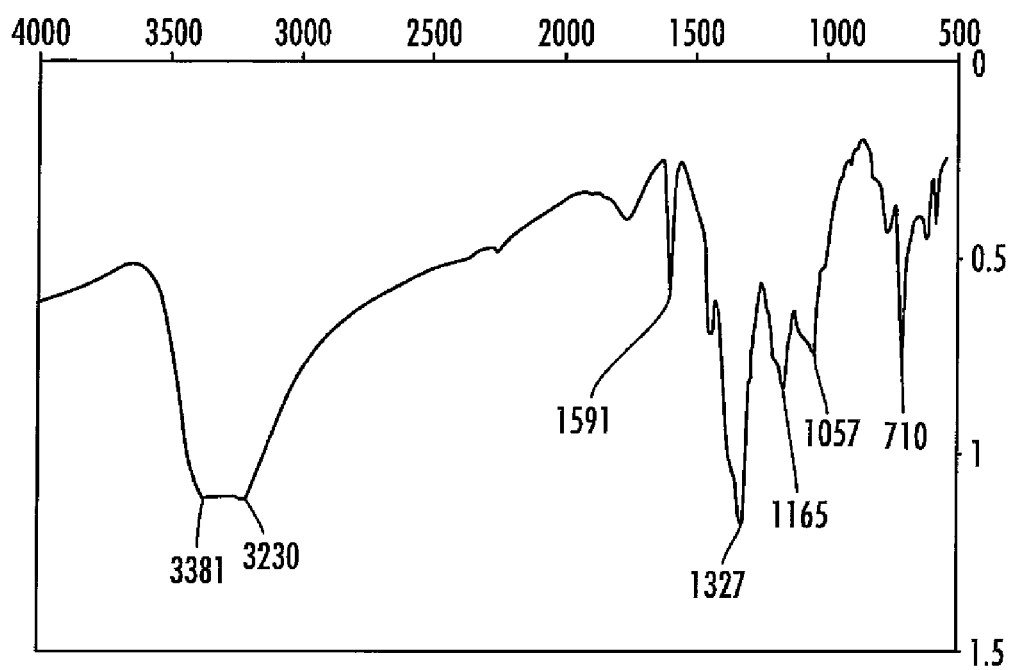

One particular reaction scheme for a polyboronic acid combined with a polydiol is illustrated in FIG. 4. In particular, in this embodiment, a triboronic acid, namely benzene-1,3,5-triboronic acid is reacted with a bis-diol, namely 1,2,4,5-tetrahydroxybenzene. As shown in FIG. 4, a covalently bonded porous network is formed.

Figure 17:
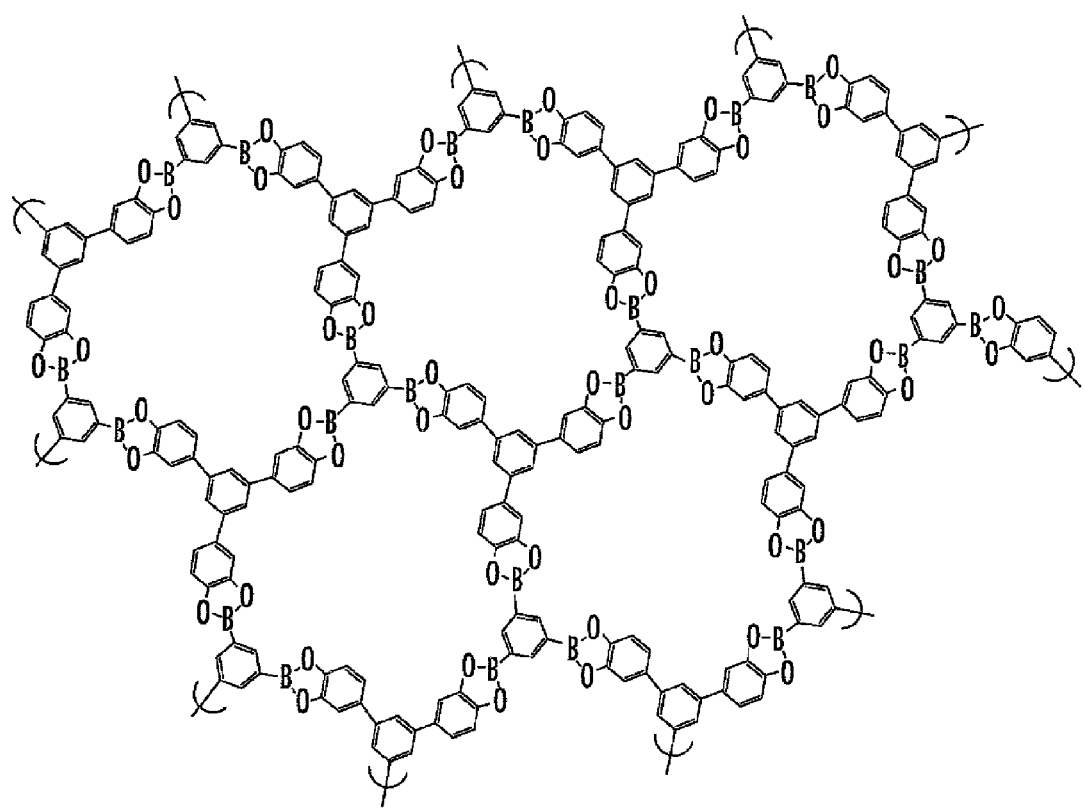
FIGS. 17 and 18 are chemical structures of porous networks that may be formed in accordance with the present disclosure.

In an alternative embodiment, the following polyboronic acid may be reacted with the following polydiol to form the structure illustrated in FIG. 17.

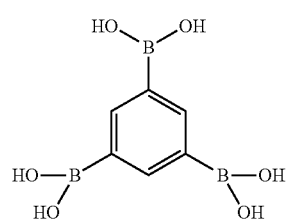

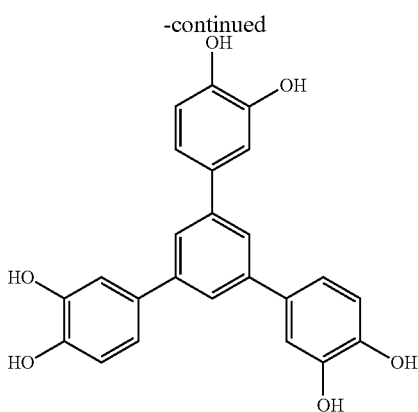

Figure 18:
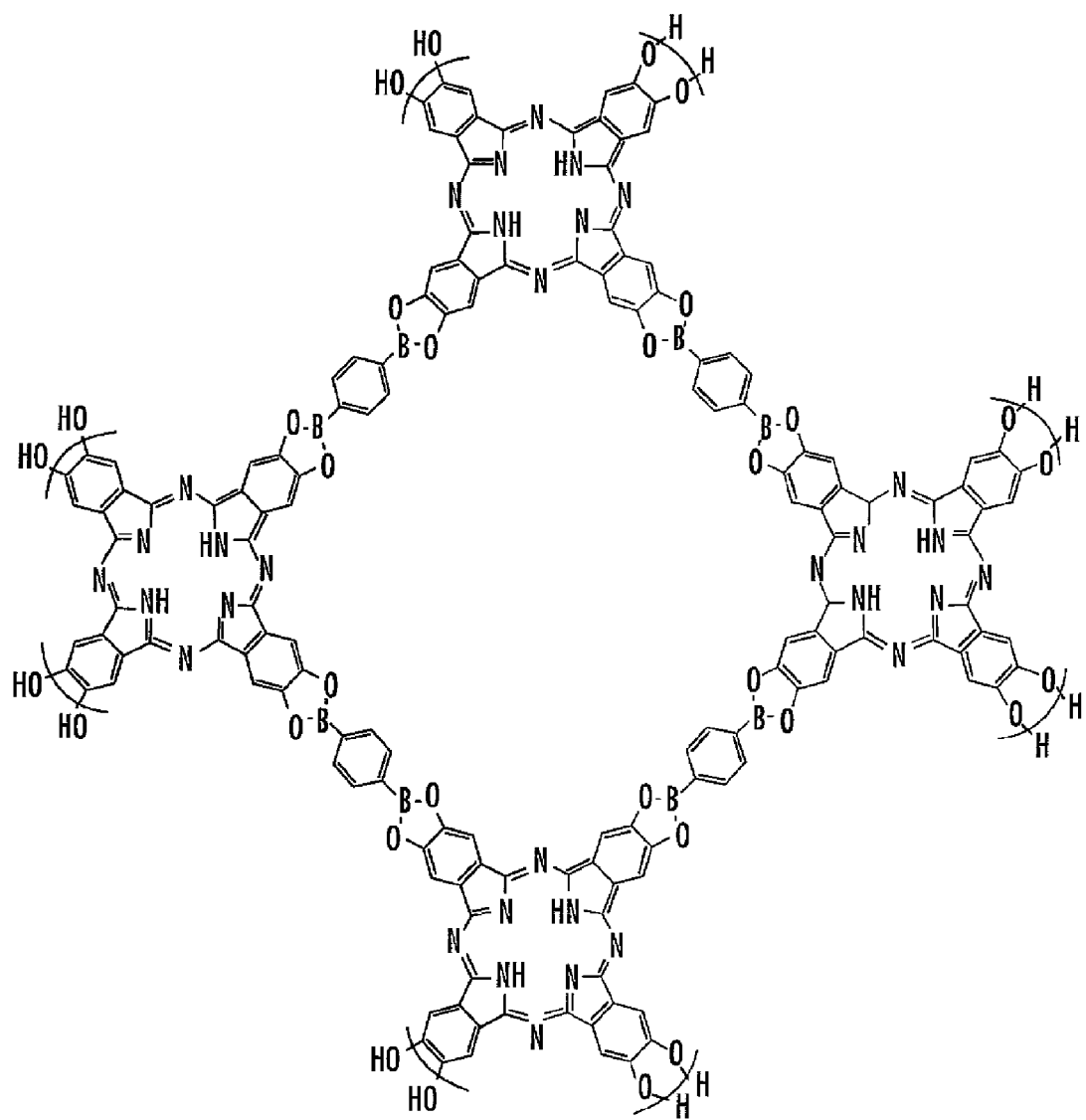

In still another embodiment, the following polyboronic acid may be combined with the following polydiol to form the structure illustrated in FIG. 18.

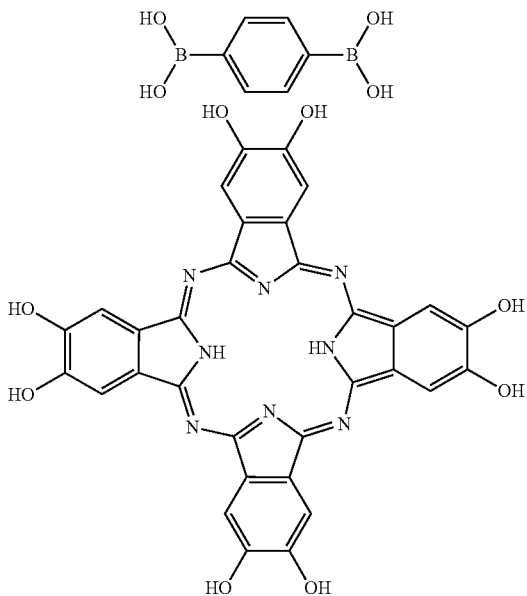

As shown by comparing FIGS. 4, 17 and 18, various different porous networks having various different properties can be formed by altering the reactants.

In addition to reacting a polyboronic acid with a polydiol, in an alternative embodiment, the polyboronic acid can be reacted with a polydiamine to form a porous network linked through diazaboroles. Examples of polydiamines that may be used include the following:

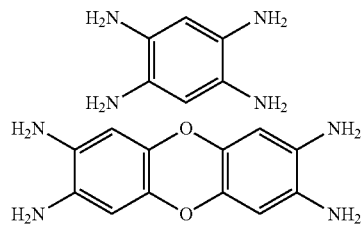

In still another embodiment, the polyboronic acid may be reacted with a polyamino alcohol in order to form a porous network linked via oxazaboroles. One example, for instance, of a polyamino alcohol is as follows:

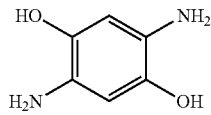

Again, by changing the nature of the second reactant, a porous network can be formed with different properties and characteristics. For instance, it is believed that a porous network formed from a polyamino alcohol may be more stable than a porous network formed from a polydiol. Porous networks linked via diazaboroles may in fact bend from planarity, raising the level of complexity in the resulting structure. Choosing between a polydiol, a polyamino alcohol, or a polydiamine may also cause changes in the affinity of the resulting porous network for particular gases and/or organic materials.

Figure 19:
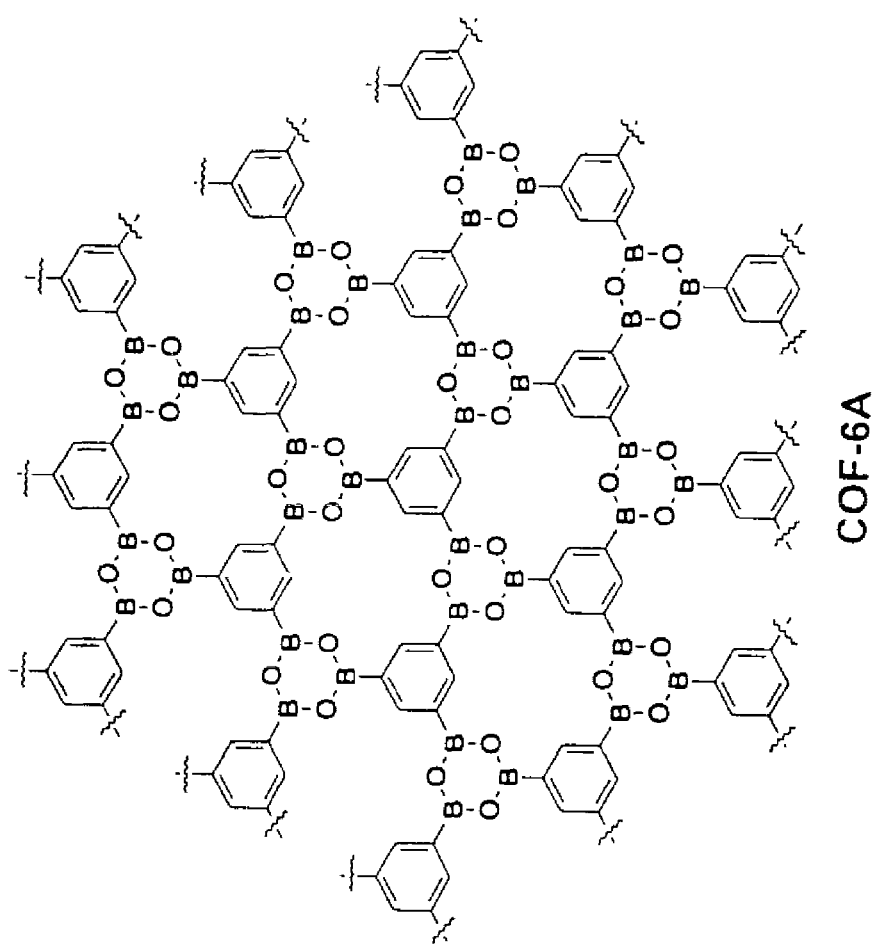
FIG. 19 is a schematic diagram of a porous network that may be made in accordance with the present disclosure.

In still another embodiment of the present disclosure, a first polyboronic acid may be reacted with a second polyboronic acid to form a porous network linked via boroxines. For example, in one embodiment, a polyboronic acid may be reacted with itself. For instance, as shown in FIG. 19, 1,3,5-triboronic acid may undergo anhydride formation to form the structure illustrated. In this embodiment, porous networks can be formed having a relatively small pore size. For instance, the pore diameter of the structure shown in FIG. 19 may be about 6 angstroms.

In addition to selecting particular reactants in order to modify and change the properties of the resulting porous network, in other embodiments, functional groups may also be incorporated into the boronate linked network. For example, functional groups may be incorporated into one or both reactants that are used to form the boronate linked network. The functional groups can be incorporated into the reactants by simple hydrogen substitution. Once incorporated into the resulting boronate linked network, the functional groups may alter the pore size of the resulting network and/or the ability of the material to adsorb gases or other organic constituents. Incorporating functional groups into the porous network may also adjust the hydrophobic or hydrophilic properties of the resulting structure. Of particular advantage, it is believed that most functional groups will not significantly alter the geometry around the borole being formed and will only have minimal impact upon ester formation. In some embodiments, the functional groups will reduce pore volume and surface area while generally increasing hydrophobicity. In some embodiments, functional groups may in fact enhance the stability of the structure. The functional groups, for instance, may protect the boronate linkages from hydrolytic degradation.

In general, any suitable functional group may be incorporated into the boronate linked network. The functional group may comprise, for instance, a carboxy group, such as an acid, an ester, or an amide, a halogen, an ether or any suitable hydrophobic group, such as an alkyl or a silyl, for example (tetramethylsilyl—TMS). It should be understood, however, that the above list is non-exhaustive and that any suitable organic functional group may be used.

In one embodiment, for instance, the boronate linked networks may be carboxy-functionalized. Incorporating carboxy groups into the porous network may bind polar species to the structure, such as volatile amines.

Figure 16:
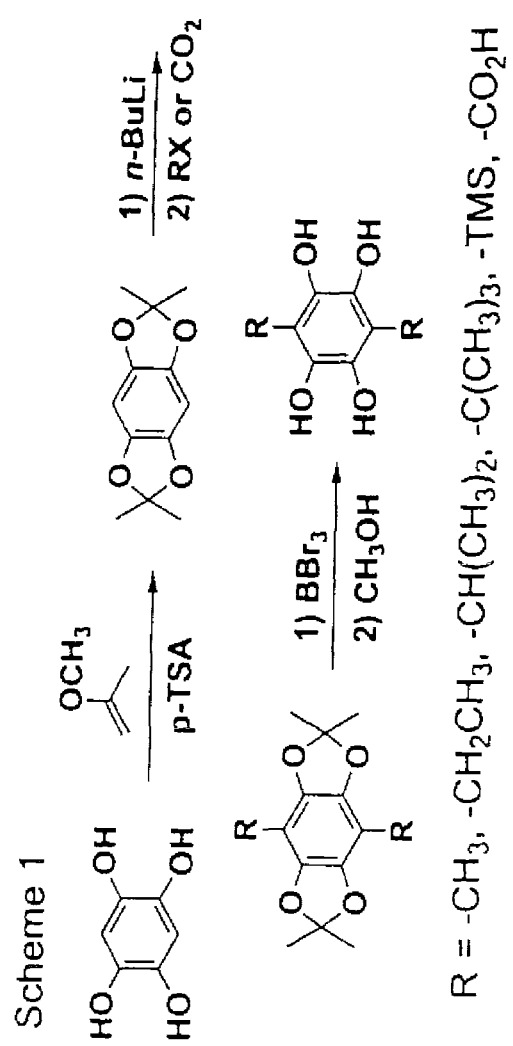
FIG. 16 is one embodiment of a reaction scheme for incorporating functional groups into a polydiol that may be used in producing a porous network in accordance with the present disclosure.

For exemplary purposes only, FIG. 16 illustrates one reaction scheme that may be used to incorporate functional groups onto a bis-diol. As shown, 1,2,4,5-tetrahydroxybenzene may be functionalized at the 3- and 6-positions with any suitable functional group, such as those listed in the figure.

As shown in FIG. 16, in one embodiment, the polydiol may first be reacted with two methoxypropene in the presence of an acid catalyst in order to initially protect the diol. In particular, acetal groups are formed. Next, deprotonation occurs using, for instance, n-butyl lithium. Functionalization results from reaction of the anion, generated by n-butyl lithium, with, for instance, an alkyl halide or carbon dioxide. The resulting carboxylic acid can be protected as the t-butyl or phenacyl ester or as an o-nitroanilide. The diol protecting group is removed with acid. After the network is formed, the ester is deprotected. Alternatively, the acid-functionalized starting material can be converted to an amide or ester. After the modification is made, the diol protecting group can be removed with an acid. Heating the t-butyl protected framework will release isobutene leaving behind the free acid. Alternatively, the phenacyl esters and o-nitroanilides protecting groups are photo-labile.

As described above, incorporating functional groups into the reactants may diminish the resulting pore volume of the porous framework. If desired, when incorporating functional groups into the boronate linked networks, longer reactants may be used to produce a proper pore size without having the pores completely clogged by the functional groups.

As described above, incorporating functional groups into one of the reactants can be done through hydrogen substitution. The following is a non-exhaustive list of reactant species that may be used to produce a boronate linked network in accordance with the present disclosure that include a functional group:

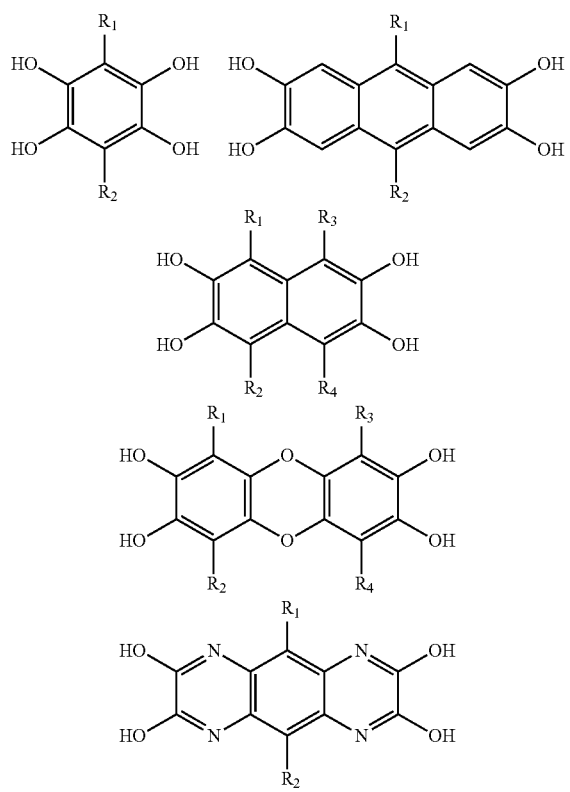

-continued

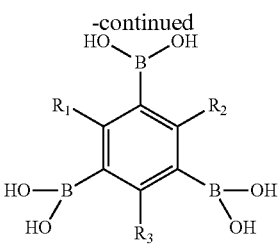

In the above formulas, $R_1$, $R_2$, $R_3$ and $R_4$ are independently hydrogen or any suitable functional group such as those described above. In certain embodiments, the same functional group may be incorporated into a reactant at multiple locations. In other embodiments, only a single functional group may be incorporated into the reactant. In still another embodiment, a reactant species may be formed containing multiple functional groups. For instance, a bis-diol may be formed as shown above wherein $R_1$ is an alkyl group and $R_2$ is hydrogen, wherein $R_1$ is TMS while $R_2$ is hydrogen, wherein $R_1$ is a carboxy group while $R_2$ is hydrogen, wherein $R_1$ is an ether while $R_2$ is a hydrogen. In other embodiments, $R_1$ and $R_2$ may both comprise functional groups that can be the same or different. For instance, in alternative embodiments, $R_1$ and $R_2$ are different alkyl groups, $R_1$ is an alkyl group and $R_2$ is a silyl group, or $R_1$ is an alkyl group and $R_2$ is a carboxy group. It should be understood that all permutations are possible.

In the above examples, only polydiols and a polyboronic acid are illustrated. It should be understood, however, that similar functional groups may also be incorporated into polydiamines and into polyamino alcohols.

As described above, porous networks can be formed according to the present disclosure having different characteristics and properties. In general, the resulting networks are highly crystalline. Pore diameters can vary depending upon many factors. In general, the diameter of the pores within the porous network can be less than about 200 angstroms, such as less than about 100 angstroms, such as less than about 50 angstroms. In one embodiment, for instance, porous networks can be formed according to the present disclosure having a pore diameter of less than about 20 angstroms.

When formed into porous sheets, the spacing between adjacent sheets can also vary. In one embodiment, the space between adjacent sheets is less than about 10 angstroms, such as from about 3 angstroms to about 5 angstroms.

Of particular advantage, porous networks made according to the present disclosure are thermally stable. For instance, porous networks can be formed that are thermally stable at temperatures of at least 400° C., such as at least 500° C.

Porous materials can be formed from the boronate linked networks that are particularly well suited for gas adsorption. Of particular advantage, gas adsorption is also reversible. The pore structures can have a surface area of greater than at least about 300 m$^2$/g, such as greater than about 1000 m$^2$/g. For instance, the surface area of the materials can be from about 300 m$^2$/g to about 2000 m$^2$/g. Micropore volume can be from about 0.1 cc/g to about 0.5 cc/g, such as from about 0.25 cc/g to about 0.35 cc/g. The above numerical ranges, however, are only exemplary for various embodiments.

Porous networks made according to the present disclosure have numerous commercial applications. For instance, since the porous network can be easily changed and varied, the resulting product can be tailored to a particular need. The ability to readily control the structure and function of the boronate linked networks allows them to be used in nanoscale materials for potential applications in the areas of separations, catalysis, optical materials, and molecular sorption in sensing. The porous networks, for instance, may find applications in gas storage, catalysis, and separations.

The present disclosure may be better understood with reference to the following example.

EXAMPLE

The following embodiment is provided to illustrate the present invention and is not intended to limit the scope of the invention.

FIG. 1 shows the synthesis of the key building block to the formation of the covalent porous network shown in FIG. 4, benzene-1,3,5-triboronic acid. First, 1,3,5-Tris(trimethylsilyl)benzene was synthesized by combining magnesium (7.77 g, 0.32 mol), dry THF (50 mL), and chlorotrimethylsilane (36.0 mL, 0.28 mol) in a round-bottom flask fitted with a reflux condenser that had previously been charged with argon. The suspension was heated to 50° C. A solution of tribromobenzene (25.0 g, 79.4 mmol) in dry THF (150 mL) was added drop-wise over a period of about 1 hour, and the reaction mixture was heated to reflux overnight. Consumption of the starting material was confirmed by TLC. The reaction mixture was cooled down to room temperature, passed though 2 inches of silica gel in a 3 inch diameter fritted funnel with hexanes, and solvents were removed under reduced pressure. The crude oil was purified by column chromatography, eluting with hexanes, to yield the pure silane (11.00 g, 37.4 mmol), a clear and colorless oil.

Next, benzene-1,3,5-triboronic acid was formed by treating the silane (9.82 g, 33.4 mmol) with neat boron tribromide (41.0 g, 0.164 mol) under argon. A condenser was attached that was also charged with argon, and the solution was heated at 100° C. for about 4 hours. Once cooled down, excess boron tribromide was distilled off under vacuum (1 Torr) at room temperature. The resulting grey-purple solid was dissolved in dry hexane (50 mL) and cooled down to 0° C. with an ice-bath. Water was slowly added drop-wise while stirring vigorously until the reaction had been fully quenched. The grey solid was collected by filtration and rinsed with water. After vacuum drying (1 torr) for 24 hours, the product was obtained in near quantitative yield. The boronic acid functional groups were capped with neopentaglycol in order to obtain further characterization data on this monomer.

Figure 2:
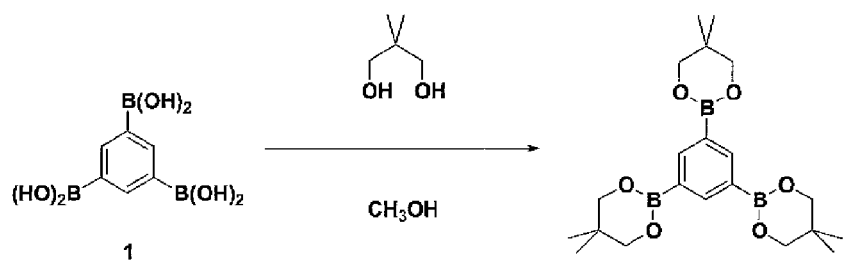
FIG. 2 is a schematic diagram for derivatizing triboronic acid for purposes of characterization.
Figure 3:
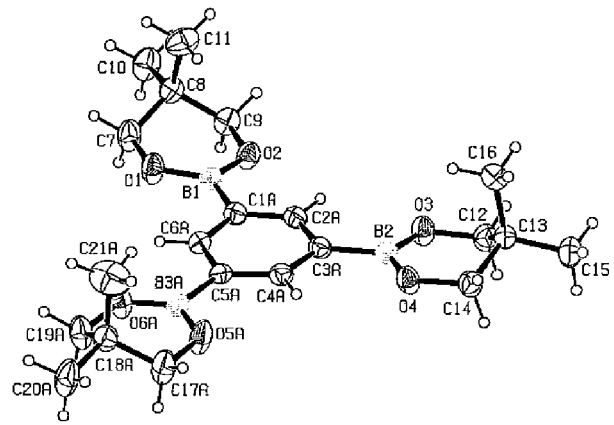
FIG. 3 are illustrations showing the crystal structure of the compound produced in FIG. 2.
Figure 3:
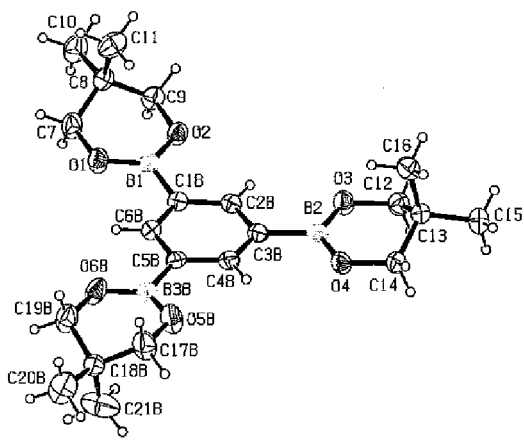

FIG. 2 shows the derivatization of benzene-1,3,5-triborinic acid to the corresponding neopentaglycol triester. To synthesize the neopentaglycol ester of benzene-1,3,5-triborinic acid, boronic acid (0.34 mmol) and neopentaglycol (116 mg, 1.11 mmol) were dissolved in methanol (2 mL). Methanol was removed under reduced pressure yielding the boronate linked networks quantitatively. The resulting white solid was recrystallized from acetonitrile, giving colorless needles. The single crystal x-ray structure is shown in FIG. 2.

FIG. 4 shows an example of the covalent porous network (CPN-1) that was readily obtained through the condensation reaction between benzene-1,3,5-triboronic acid 1 and 1,2,4,5-tetrahydroxybenzene 2 in 2% methanol/THF by refluxing under a constant flow of nitrogen for about 72 hours. After cooling to room temperature, the resulting fine solid was collected by filtration, washed with copious amounts of THF, and dried under vacuum (1 Torr) at about 70° C. for about 72 hours to afford 96% yield of CPN-1 as a fine white powder.

Figure 7:
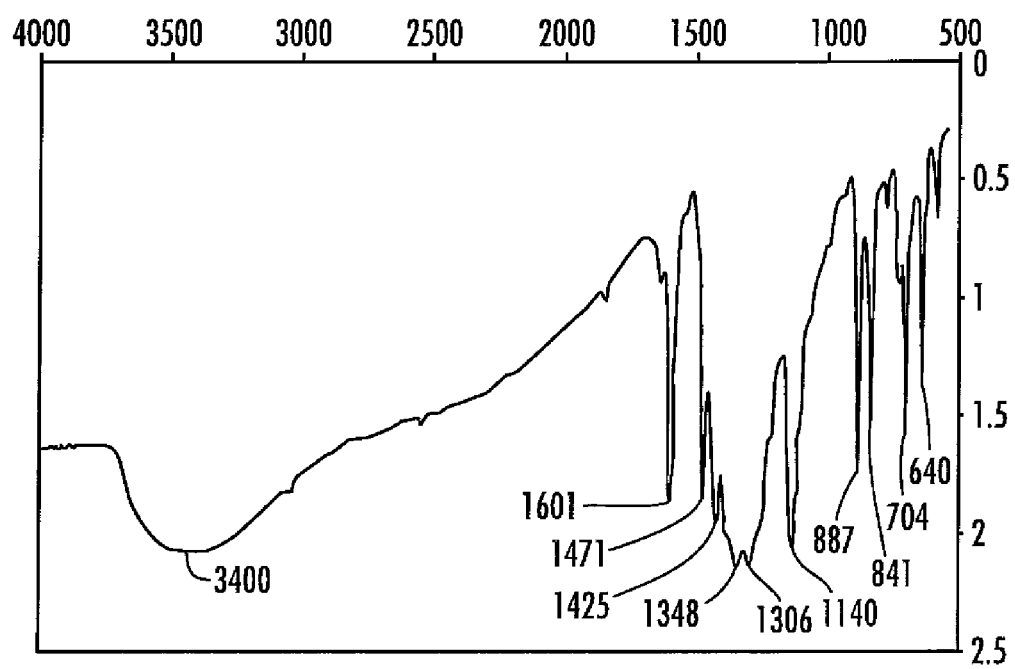

CPN-1 was characterized using FTIR, $^{11}$B and $^1$H NMR to confirm that the expected building blocks were indeed present in the assembly and that the desired bonds were formed. Infrared analysis of this material, as shown in FIG. 7, shows a significant attenuation for the hydroxyl stretch compared to the starting materials indicating that a dehydration reaction did in fact proceed. Furthermore, two intense peaks around 1300 and 1345 $cm^{-1}$ signify that the boronate linked network functionality is present while peaks indicative of boron anhydride (boroxine) formation, namely a broad, intense peak at 1350 and a sharp peak at 580 $cm^{-1}$, were absent. Solid-state $^{11}$B NMR analysis confirmed the presence of trigonal planar boron centers revealing a single peak at 30 ppm compared to the starting boronic acid monomer which appears at 25 ppm. To verify that both monomers were incorporated into the network, $^1$H NMR analysis was performed using 1 M KOH in $D_2O$ as the solvent. Under these basic conditions the boronate linked material is hydrolyzed, providing a simple quantitative method to measure the composition in solution. Comparing the spectrum of degraded CPN-1 with starting materials confirms the presence of both monomers in the network. Integration verifies that the bis-diol and tri-boronic acid are present in the expected 3:2 ratio.

Figure 11:
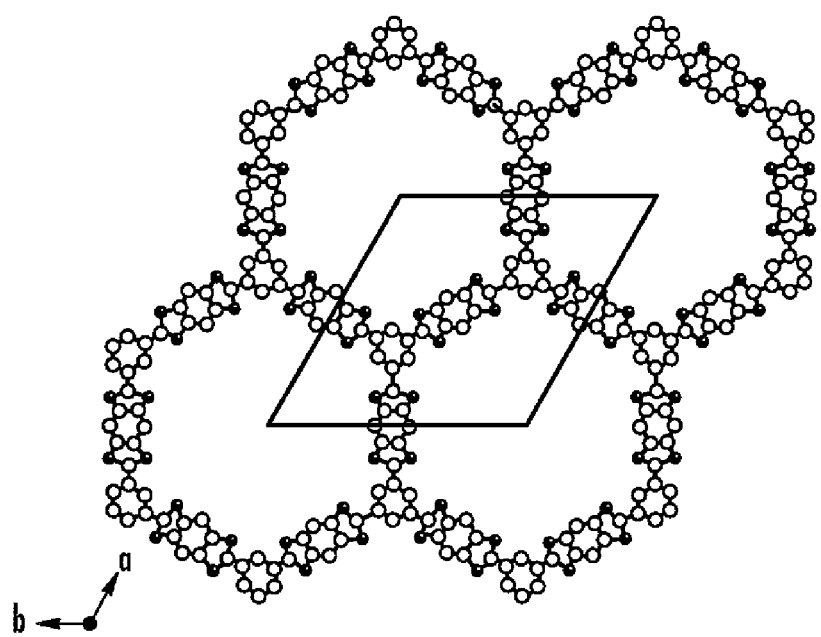
Figure 12:
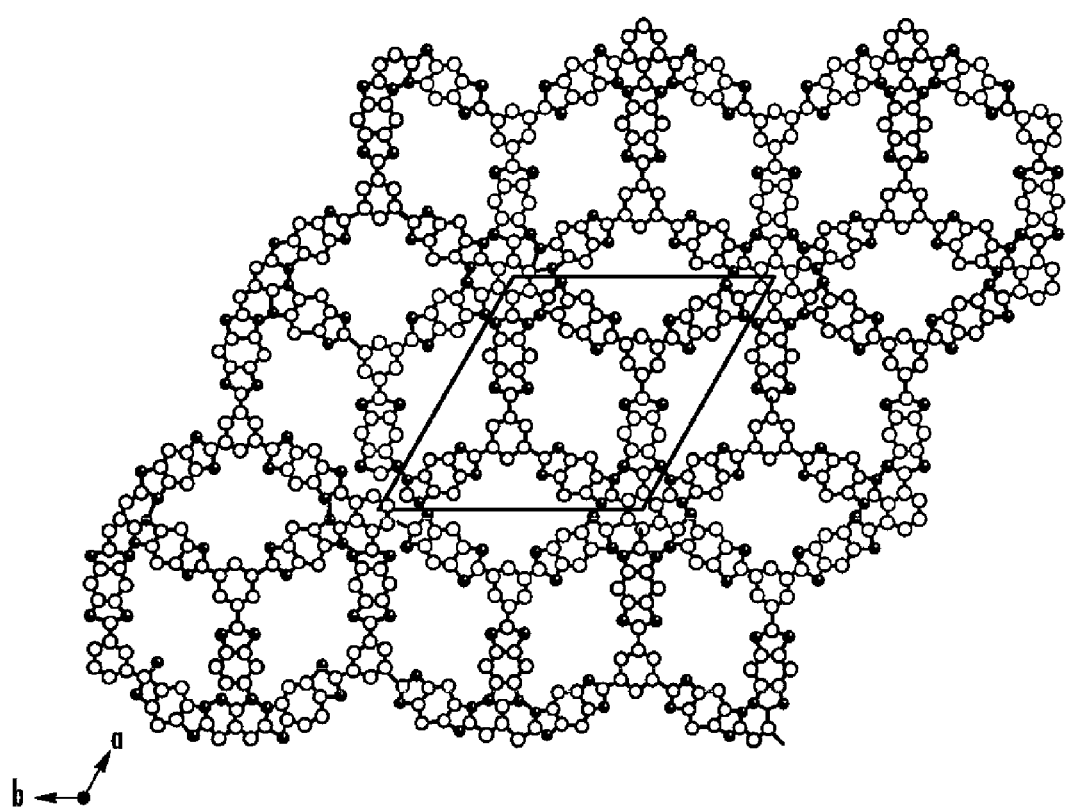
Figure 13:
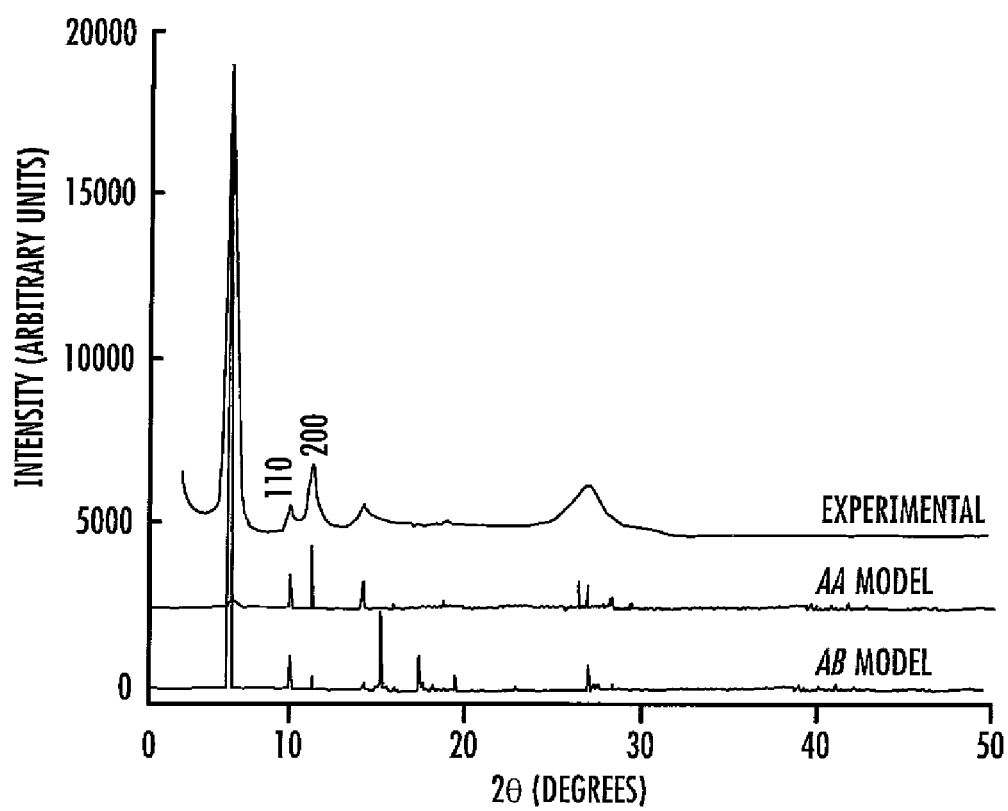

Powder X-ray diffraction (PXRD) analysis shows the formation of a highly crystalline network. In order to evaluate the structure of the network formed, the possible assemblies were modeled using Macromodel. The proposed network contains pores with a diameter of approximately 18 Å. In conjunction with crystallographic data for analogous model compounds, Diamond software was used to define a unit cell with the origin located in the center of the pore. Based on these lattice parameters, expected powder diffraction patterns were generated assuming that the tri-boronic acid and bis-diol building blocks assembled as proposed. Planar two-dimensional sheets were expected and the manner in which these sheets can stack is limited. The most likely crystal packing allows the sheets to assemble in a registered AA manner where atoms in adjacent sheets lie directly over each other forming large cavities and leaving a hexagonal array of 1D, 18 Å pores (FIG. 11); alternatively they could assemble in a staggered AB arrangement, where the sheets offset by ½, ½ placing the phenyl rings in every other layer in registry while partially blocking the pore of the intermediate layer (FIG. 12). Although both models have primitive hexagonal symmetry, they would display distinct diffraction patterns (FIG. 13).

Figure 14:
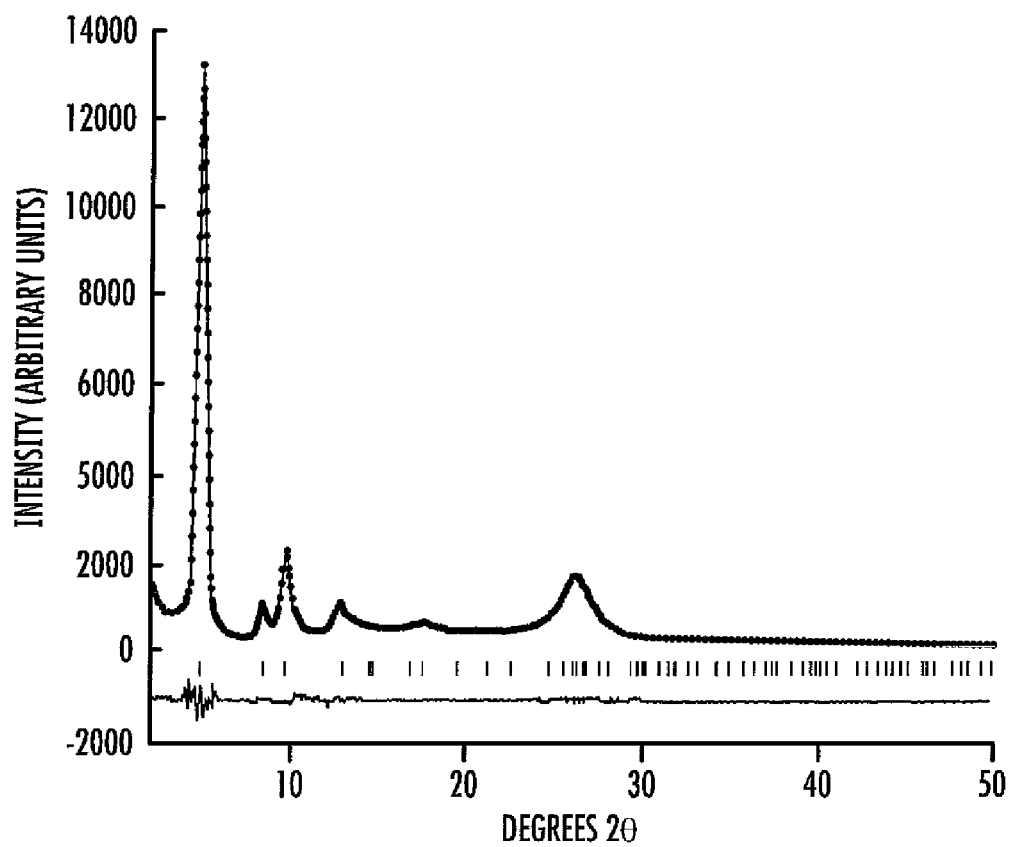

There are too few peaks observed in the PXRD of CPN-1 to use the Rietveld method to refine atomic positions; however, the LeBail routine can be used (FIG. 14) to compare calculated and experimental PXRD patterns in order to determine the most probable structural motif. In FIG. 13, the experimental powder diffraction pattern is compared with the calculated patterns generated using the atomic positions determined from Diamond. There is substantial correlation between the expected peak position and intensities for the registered AA model and the experimental data, whereas the projected pattern for the staggered AB arrangement does not fit experimental data. Consistent with the modeled structure, the PXRD supports the presence of 18 Å micropores, arranged in a hexagonal orientation. The interlayer spacing between sheets from modeling versus that found from the PXRD analysis agree well (3.597 Å calc. versus 3.385 Å exp.).

Figure 8:
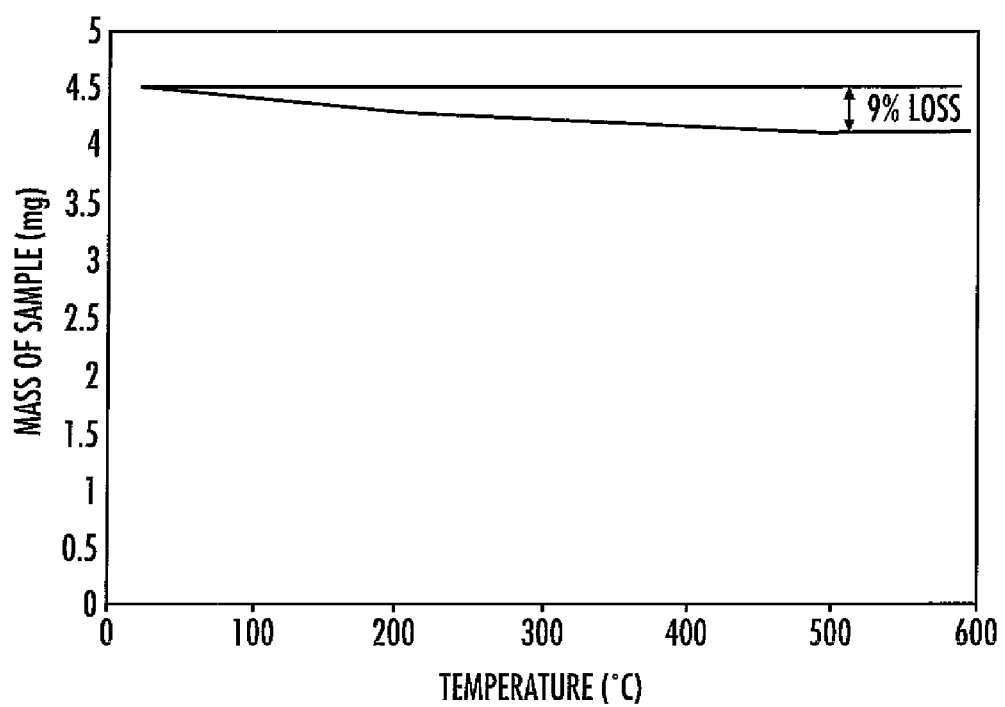
Figure 9:
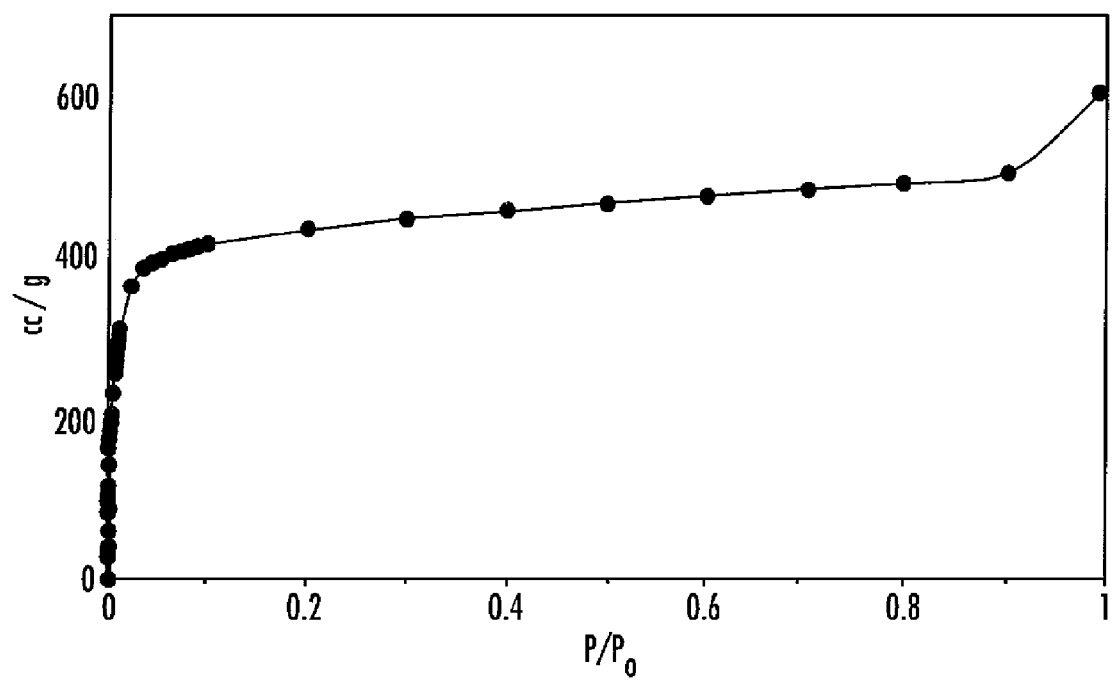
Figure 10:
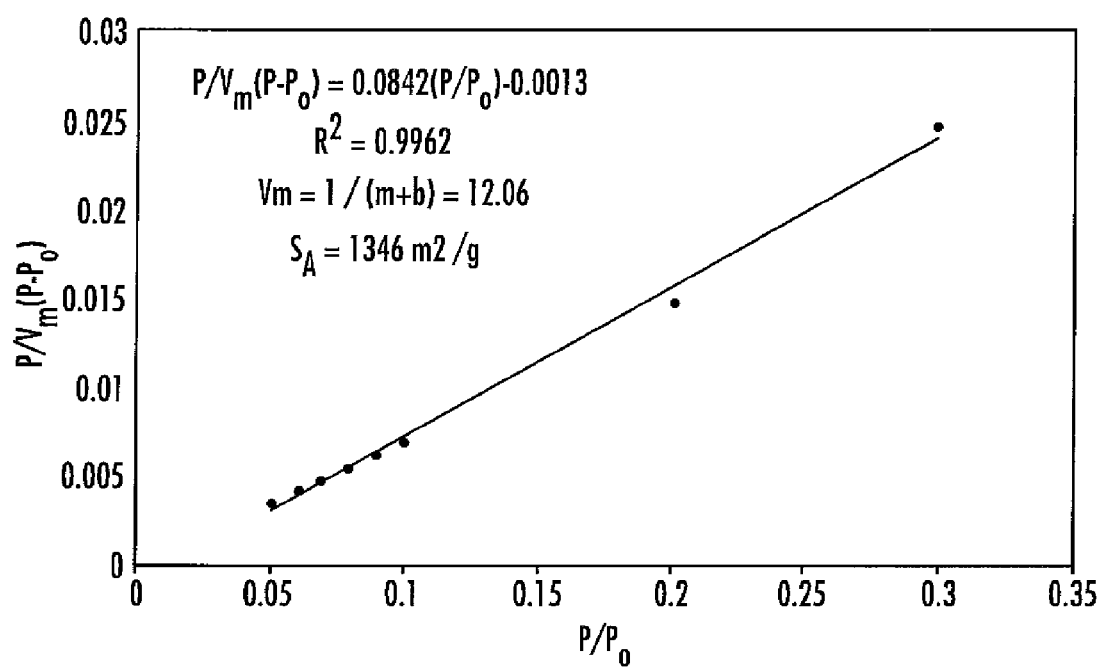

The porosity and pore stability of CPN-1 were evaluated by measuring the $N_2$ gas adsorption. This material exhibits thermal stability to temperatures up to 500° C., as shown by thermogravimetric analysis (FIG. 8). As such, a sample of CPN-1 was evacuated under dynamic vacuum ($10^{-5}$ Torr) while heated at 400° C. for about 2.5 hours. This sample was used for gas adsorption measurements from 0 to 760 Torr at 77 K. The adsorption profile was reversible and reproducible and showed a very sharp uptake at low partial pressure (P/Po from $4\times10^{-6}$ to 0.01) which is indicative of microporous material (FIG. 9). Using the BET model (FIG. 10), the apparent surface area was determined to be about 1350 m$^2$/g, which corresponds to a micropore volume of about 0.29 cm$^3$/g (FIG. 10).

In summary, the present invention is a novel method of synthesizing and characterizing a microporous, covalently-linked, poly(boronate) network with persistent pores. Spectral characterization has confirmed the bonding motif to generate infinite 2D porous sheets while PXRD was used to define the long range ordering of these sheets, such that atoms in adjacent layers lie directly over each other resulting in a hexagonal array of 1D, 18 nm pores. The resulting Covalent Porous Network (CPN) is thermally stable to 500° C. and maintains a higher surface area than most known porous materials. Given the enhanced stability, high surface area and small micropore volume, this CPN appears ideally suited to serve as a matrix for gas adsorption.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A process for forming a boroxine linked porous network comprising:
   reacting a polyboronic acid or an acyclic boronate ester thereof with itself to form an anhydride porous network.

2. The process as defined in claim 1, the porous network defining pores having a pore diameter of less than about 200 angstroms.

3. The process as defined in claim 1, wherein the polyboronic acid or an acyclic boronate ester thereof comprises a triboronic acid or an acyclic boronate ester thereof.

4. The process as defined in claim 3, wherein the triboronic acid comprises benzene-1,3,5-triboronic acid or an acyclic boronate ester thereof.

5. The process as defined in claim 1, wherein the polyboronic acid or an acyclic boronate ester thereof comprises a triboronic acid.

6. The process as defined in claim 1, wherein the polyboronic acid or an acyclic boronate ester thereof comprises:

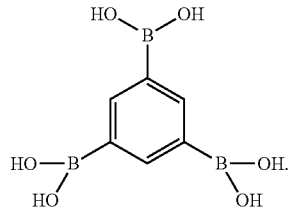 [SMILES: OB(O)c1cc(B(O)O)cc(B(O)O)c1]

7. The process as defined in claim 1, wherein the boroxine has the following structure:

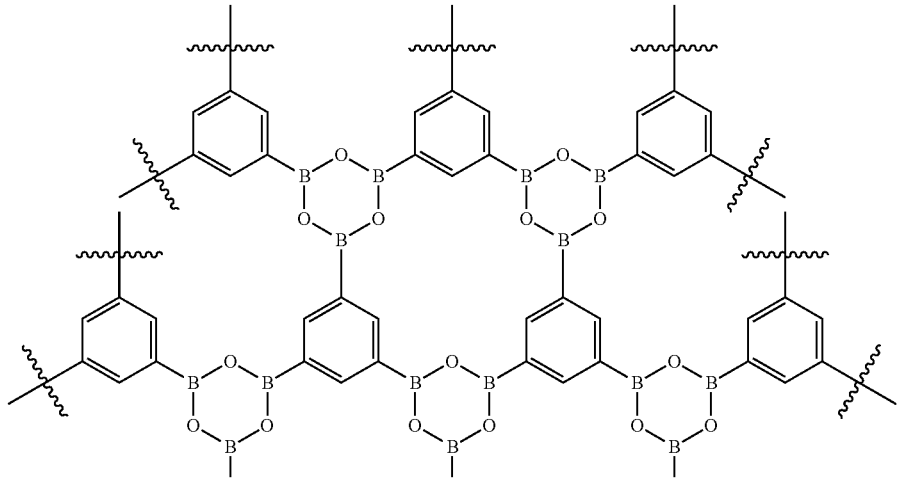

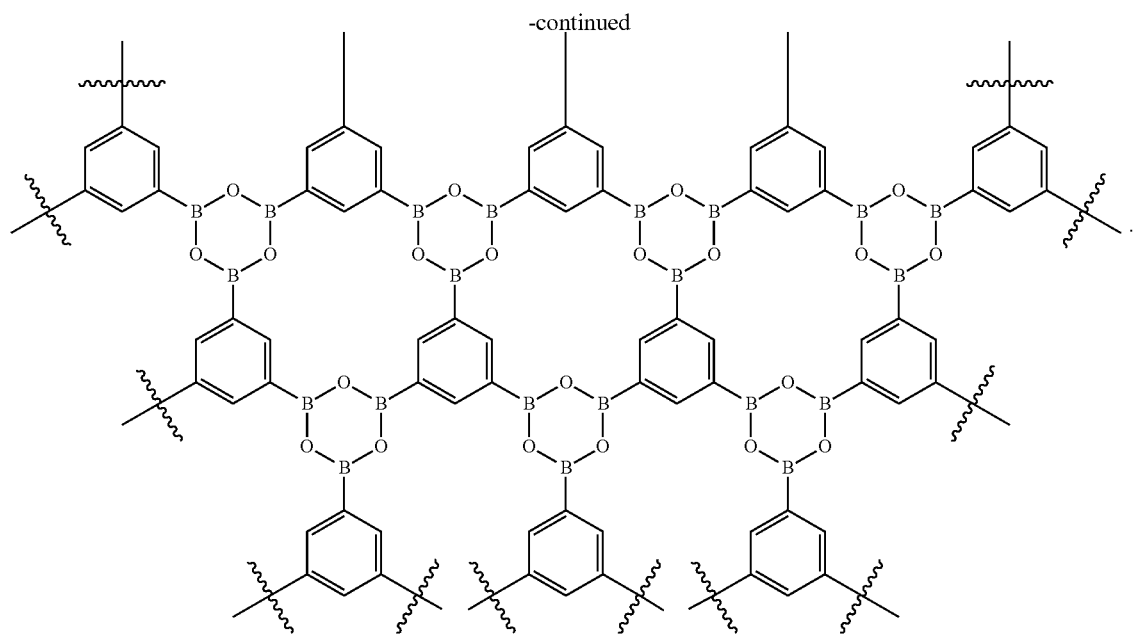
8. The process as defined in claim 1, wherein the polyboronic acid or an acyclic boronate ester thereof comprises:
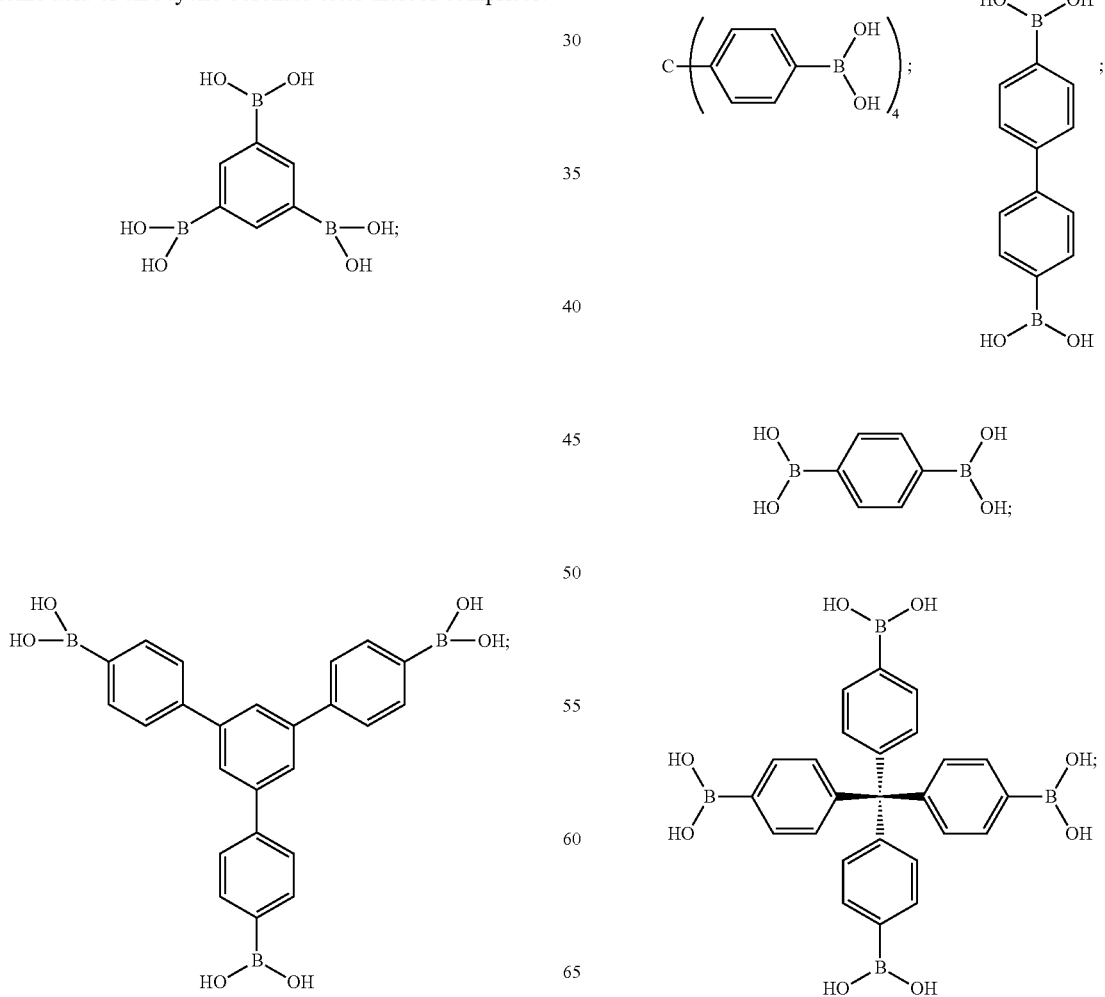

-continued
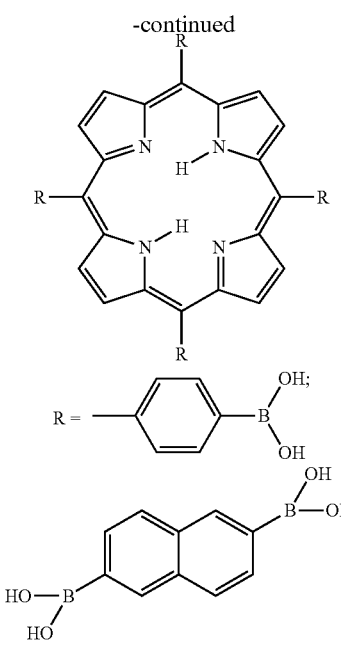
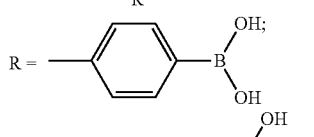
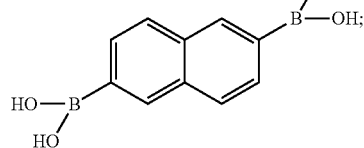
or an acyclic boronate ester thereof.
* * * * *